United States Patent
Stark

(10) Patent No.: US 6,175,119 B1
(45) Date of Patent: Jan. 16, 2001

(54) PHOTOMULTIPLIER TUBE IDENTIFIER

(75) Inventor: Iain Stark, Nepean (CA)

(73) Assignee: IS²Research Inc., Ontario (CA)

(*) Notice: Under 35 U.S.C. 154(b), the term of this patent shall be extended for 0 days.

(21) Appl. No.: 09/127,987

(22) Filed: Aug. 3, 1998

(30) Foreign Application Priority Data

Aug. 1, 1997 (CA) .................................................. 2212196

(51) Int. Cl.⁷ ..................................................... G01T 1/20
(52) U.S. Cl. ...................... 250/369; 250/367; 250/363.09
(58) Field of Search ............................. 250/369, 363.09, 250/367, 363.07, 363.03

(56) References Cited

U.S. PATENT DOCUMENTS

| | | |
|---|---|---|
| 3,777,161 * 12/1973 | Lee | ........................ 250/367 |
| 3,900,731 8/1975 | Chevalier et al. . | |
| 3,911,278 * 10/1975 | Stout | .................... 250/369 |
| 4,047,034 9/1977 | Auphan . | |
| 4,079,257 3/1978 | Jatteau et al. . | |
| 4,272,677 6/1981 | Berthold et al. . | |
| 4,516,025 5/1985 | Yamakawa et al. . | |
| 4,517,460 5/1985 | Meulenbrugge et al. . | |
| 4,583,187 4/1986 | Stoub . | |
| 4,605,856 8/1986 | Persyk et al. . | |
| 4,611,117 9/1986 | Seibert et al. . | |
| 4,882,495 11/1989 | Tanaka . | |
| 5,004,904 4/1991 | Yamakawa et al. . | |
| 5,237,173 8/1993 | Stark et al. . | |
| 5,525,803 * 6/1996 | Watanabe et al. | .................... 250/369 |
| 5,576,546 * 11/1996 | Gagnon | ................. 250/369 |
| 5,646,408 * 7/1997 | Goldberg et al. | ............... 250/363.07 |

FOREIGN PATENT DOCUMENTS 0 066 763 A1 12/1982 (EP) .
0 450 388 B1 10/1991 (EP) .

* cited by examiner

Primary Examiner—Constantine Hannaher
Assistant Examiner—Otilia Gabor
(74) Attorney, Agent, or Firm—Finnegan, Henderson, Farabow, Garrett & Dunner, L.L.P.

(57) ABSTRACT

A photomultiplier tube identifier is designed to identify a malfunctioning photomultiplier tube in a scintillation camera having an array of photomultiplier tubes. The photomultiplier tube identifier includes a photomultiplier tube for generating a photomultiplier tube signal. An amplifier/integrator generates an amplified/integrated signal from the photomultiplier tube signal. An analog to digital converter generates a digitized signal from the amplified/integrated signal. A series of pull up resistors generates a code signal identifying the photomultiplier tube. A bus buffer generates an encoded signal comprising the amplified/integrated signal followed by the code signal. A position computing device calculates the position of the photomultiplier tube. An image computer generates an image from a plurality of encoded signals. A display displays the image.

15 Claims, 13 Drawing Sheets

PHOTOMULTIPLIER TUBE IDENTIFIER

FIELD OF INVENTION

The present invention relates to a photomultiplier tube identifier. In particular, the invention relates to a method and apparatus for identifying a malfunctioning photomultiplier tube in a scintillation camera.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In order to operate a scintillation camera as described above, the patient should be supported horizontally on a patient support or stretcher.

The detector head of the scintillation camera must be able to pass underneath the patient. Therefore, in order for the scintillation camera to generate images from underneath the patient, the patient support must be thin. However, detector heads are generally supported by a pair of arms which extend from a gantry. Thus, the patient support generally must be cantilevered in order for the detector head to be able to pass underneath the patient without contacting any supporting structure associated with the patient support. The design of a cantilevered patient support that is thin enough to work properly with a scintillation camera is exceedingly difficult. Expensive materials and materials that are difficult to work with, such as carbon fibre, are often used in the design of such cantilevered patient supports.

A certain design of gantry or support structure for a scintillation camera includes a frame upon which a vertically oriented annular support rotates. Extending out from the rotating support is an elongate support. The elongate generally comprises a pair of arms. The pair of arms generally extends through a corresponding pair of apertures in the rotating support. One end of the pair of arms supports the detector head on one side of the annular support. The other end of the pair of arms supports a counter balance weight. Thus, the elongate support is counterbalanced with a counterweight on the opposite side of the detector head.

With such a design of support structure for a scintillation camera, a patient must lie on a horizontally oriented patient support. The patient support must be cantilevered so that the detector head can pass underneath the patient. If the detector head must pass underneath only one end of the patient, such as the patient's head, the cantilevered portion of the patient support is not long enough to cause serious difficulties in the design of the cantilevered patient support. However, if the camera must be able to pass under the entire length of the patient, the entire patient must be supported by the cantilevered portion of the patient support. As the cantilevered portion of the patient support must be thin so as not to interfere with the generation of images by the scintillation camera, serious design difficulties are encountered.

Among the advantages associated with such as design of support structure is that a patient may be partially pass through the orifice defined by the annular support so that the pair of arms need not be as long. However, the patient support must be able to support the patient in this position relative to the annular support, must be accurately positionable relative to the annular support, and must not interfere either with the rotation of the annular support or with the cables which will inevitably extend from the detector head to a nearby computer or other user control.

The photomultiplier tubes in a scintillation camera generate electric signals. The signals are processed, and images are created corresponding to the radiation emitted by the patient.

From time to time, images are generated that contain one or more artifacts or flaws. Artifacts are often caused by one or more malfunctioning photomultiplier tubes. A malfunctioning photomultiplier tube may be generating incorrect signals, may be generating no signal at all, or the processing of the signals from a particular photomultiplier tube may not be being properly processed.

To determine the cause of the artifact and then correct the artifact, it is important to identify all malfunctioning photomultiplier tubes. However, inspecting and testing photomultiplier tubes is difficult, time consuming and expensive.

SUMMARY OF THE INVENTION

An object of the invention is to provide an improved method and apparatus for identifying photomultiplier tubes.

A second object of the invention is to provide a method and apparatus for identifying malfunctioning photomultiplier tubes that is convenient to use, fast and inexpensive.

The invention relates to a photomultiplier tube identifier for identifying a malfunctioning photomultiplier tube in a scintillation camera having an array of photomultiplier tubes. The photomultiplier tube identifier includes a photomultiplier tube for generating a photomultiplier tube signal. The photomultiplier tube identifier also includes means for generating a code signal identifying the photomultiplier tube. A bus buffer generates an encoded signal comprising the photomultiplier tube signal followed by the code signal. A position computing device calculates the position of the photomultiplier tube. An image computer generates an image from a plurality of encoded signals. A display displays the image.

The invention also relates to a method for identifying a malfunctioning photomultiplier tube in a scintillation camera having an array of photomultiplier tubes. The method includes the steps of: generating a photomultiplier tube signal; generating a code signal identifying the photomultiplier tube; generating an encoded signal comprising the photomultiplier tube signal followed by the code signal; calculating the position of the photomultiplier tube; generating an image from a plurality of encoded signals; displaying the image.

An embodiment of the invention relates to a photomultiplier tube identifier for identifying a malfunctioning photomultiplier tube in a scintillation camera having an array of photomultiplier tubes. The photomultiplier tube identifier includes a photomultiplier tube for generating a photomultiplier tube signal. An amplifier/integrator generates an amplified/integrated signal from the photomultiplier tube signal. An analog to digital converter generates a digitized signal from the amplified/integrated signal. A series of pull up resistors generates a code signal identifying the photomultiplier tube. A bus buffer generates an encoded signal comprising the amplified/integrated signal followed by the code signal. A position computing device calculates the position of the photomultiplier tube. An image computer generates an image from a plurality of encoded signals. A display displays the image.

Advantageously, the invention provides a method and apparatus for identifying malfunctioning photomultiplier tubes that is convenient to use, fast and inexpensive.

Other advantages, objects and features of the present invention will be readily apparent to those skilled in the art from a review of the following detailed description of preferred embodiments in conjunction with the accompanying drawings and claims.

BRIEF DESCRIPTION OF THE DRAWINGS

The embodiments of the invention will now be described with reference to the accompanying drawings, in which.

Figure 1:
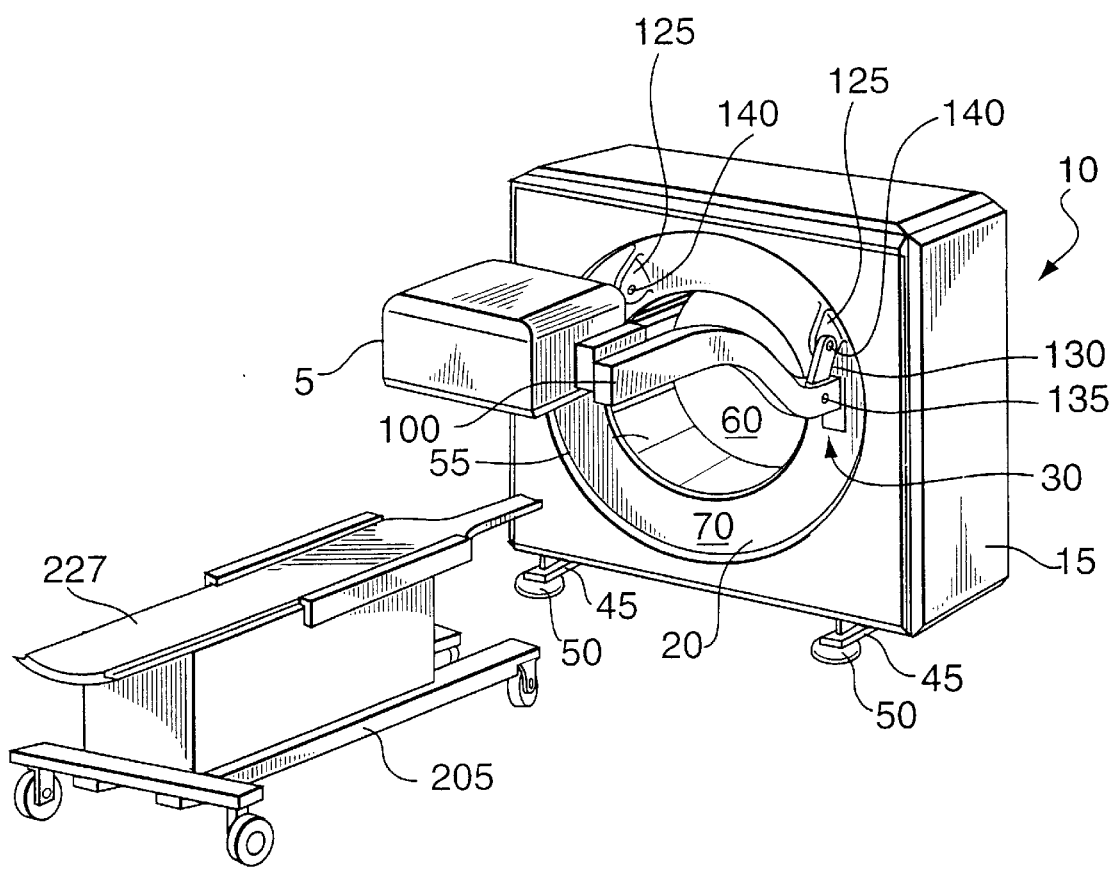
FIG. 1 is a perspective view of a scintillation camera including a detached patient support in accordance with the invention.
Figure 2:
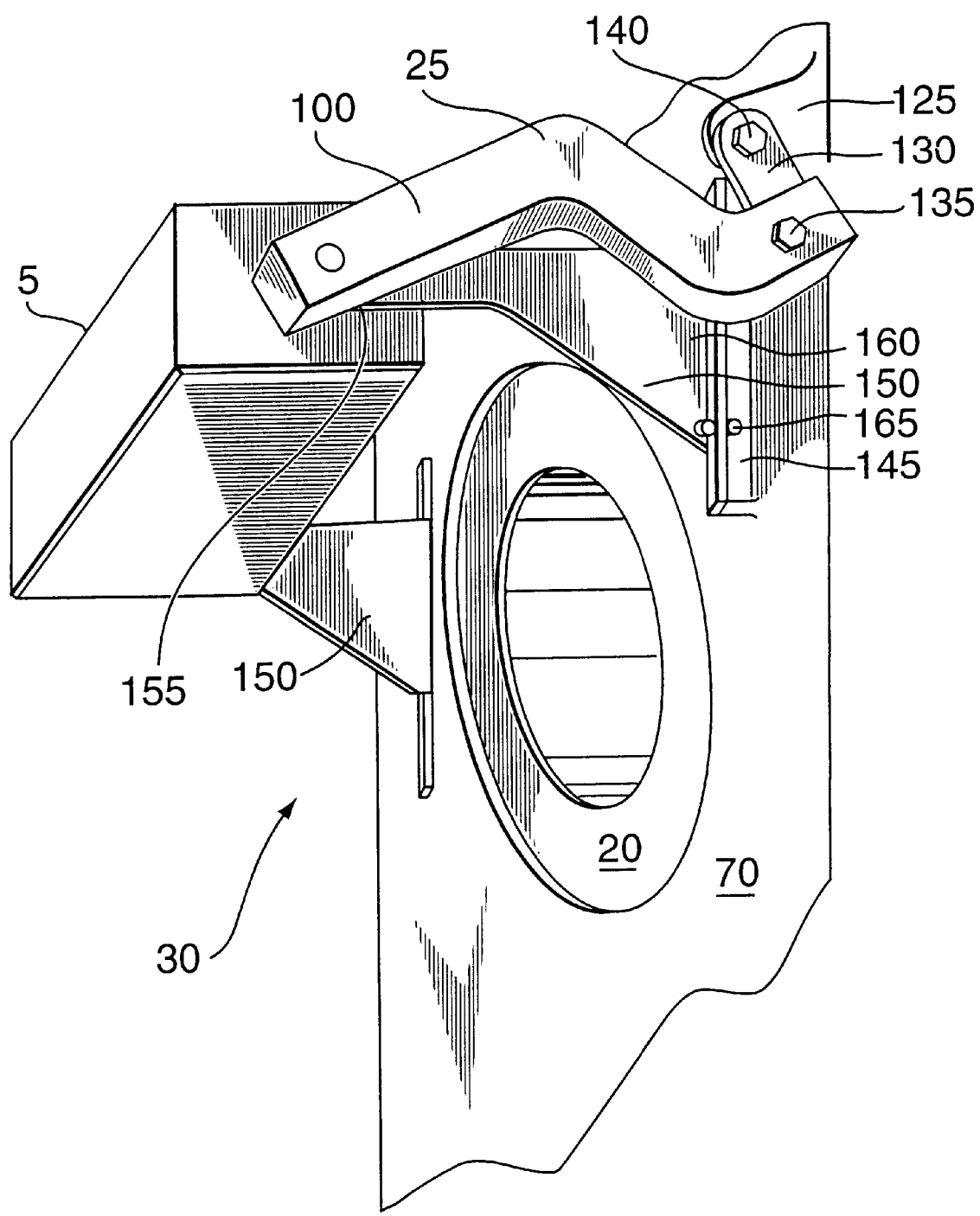
FIG. 2 is a perspective view of the guide of a scintillation camera.
Figure 3:
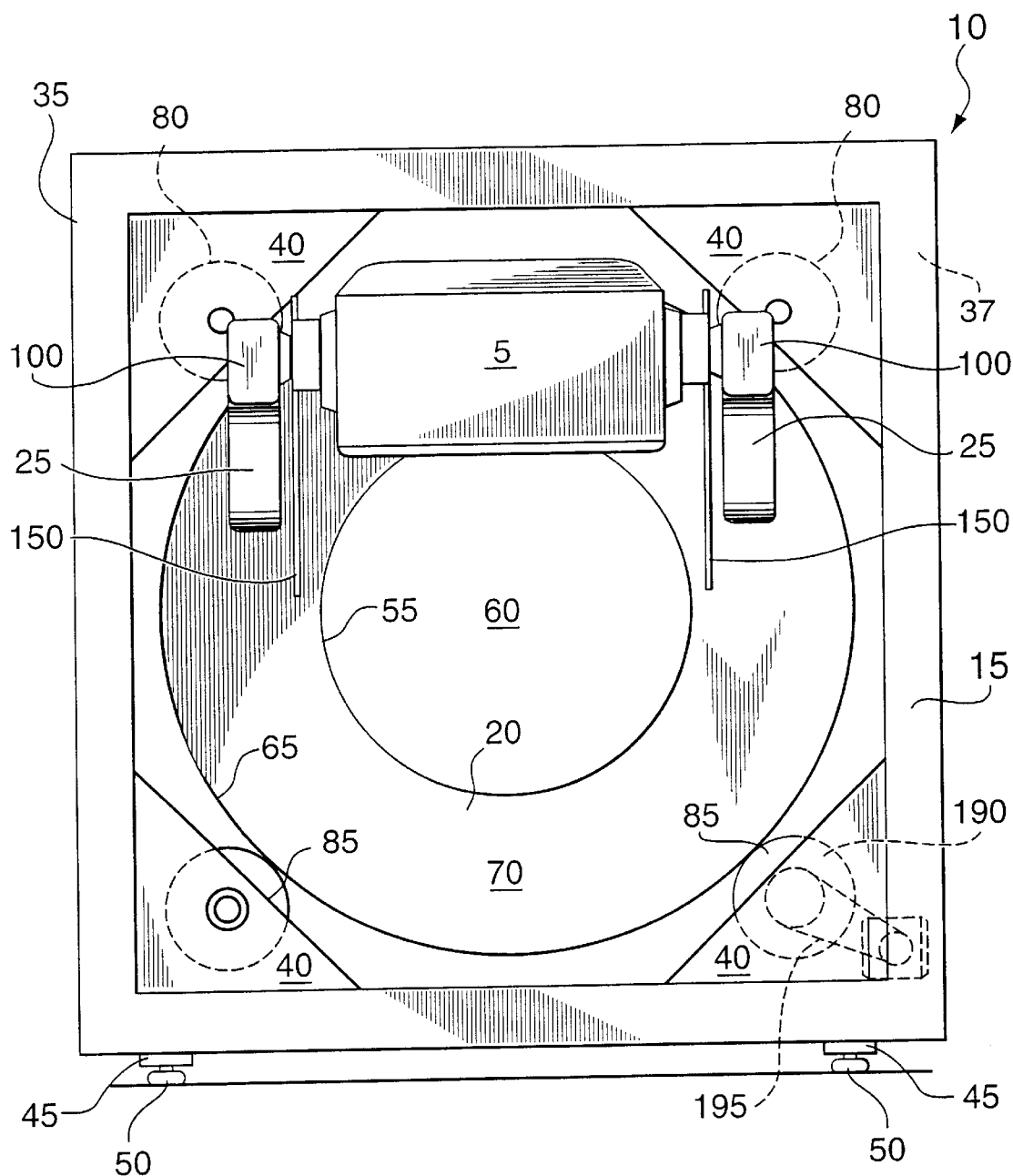
FIG. 3 is a front elevation view of a scintillation camera.
Figure 4:
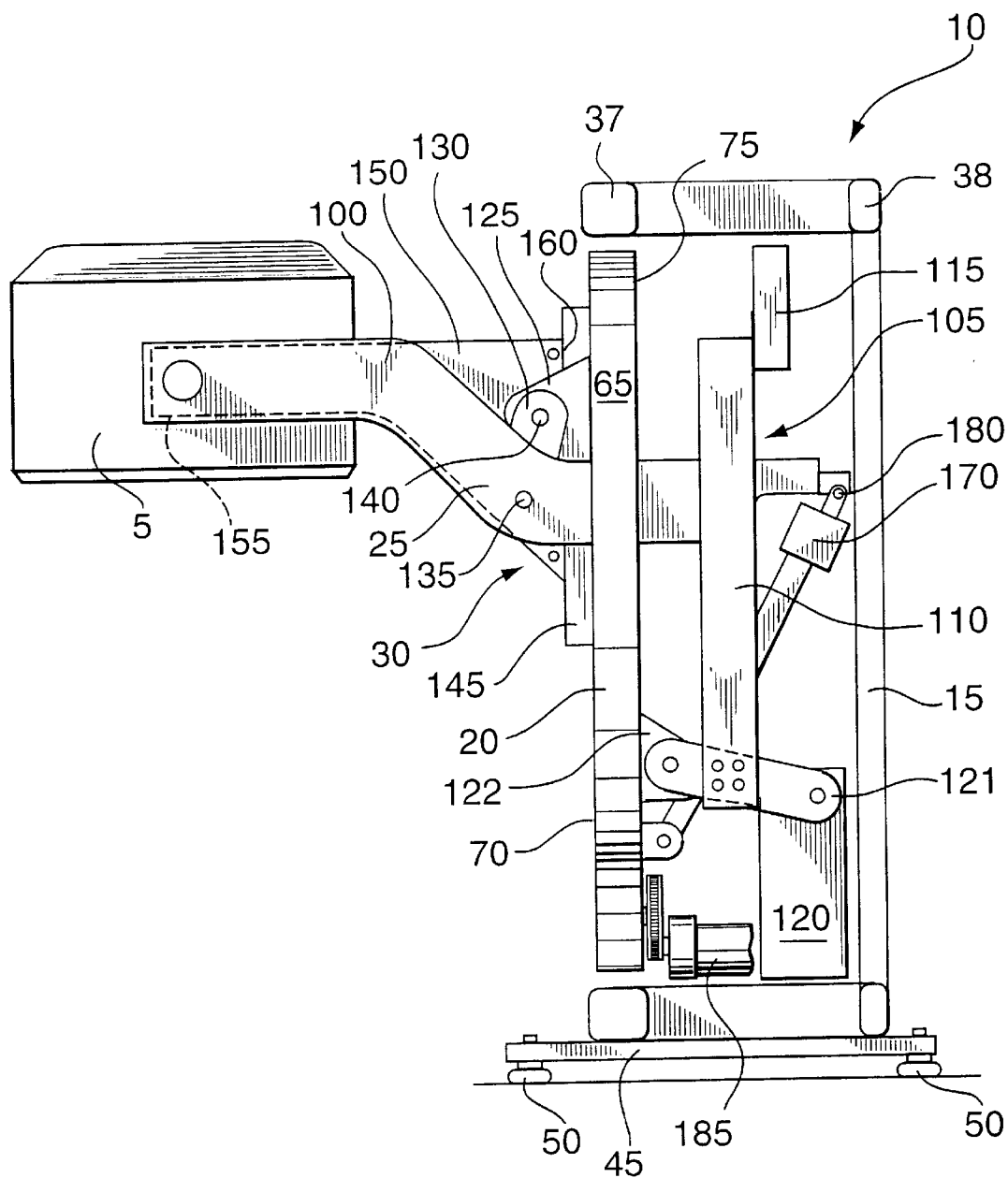
FIG. 4 is a side elevation view of a scintillation camera.
Figure 5:
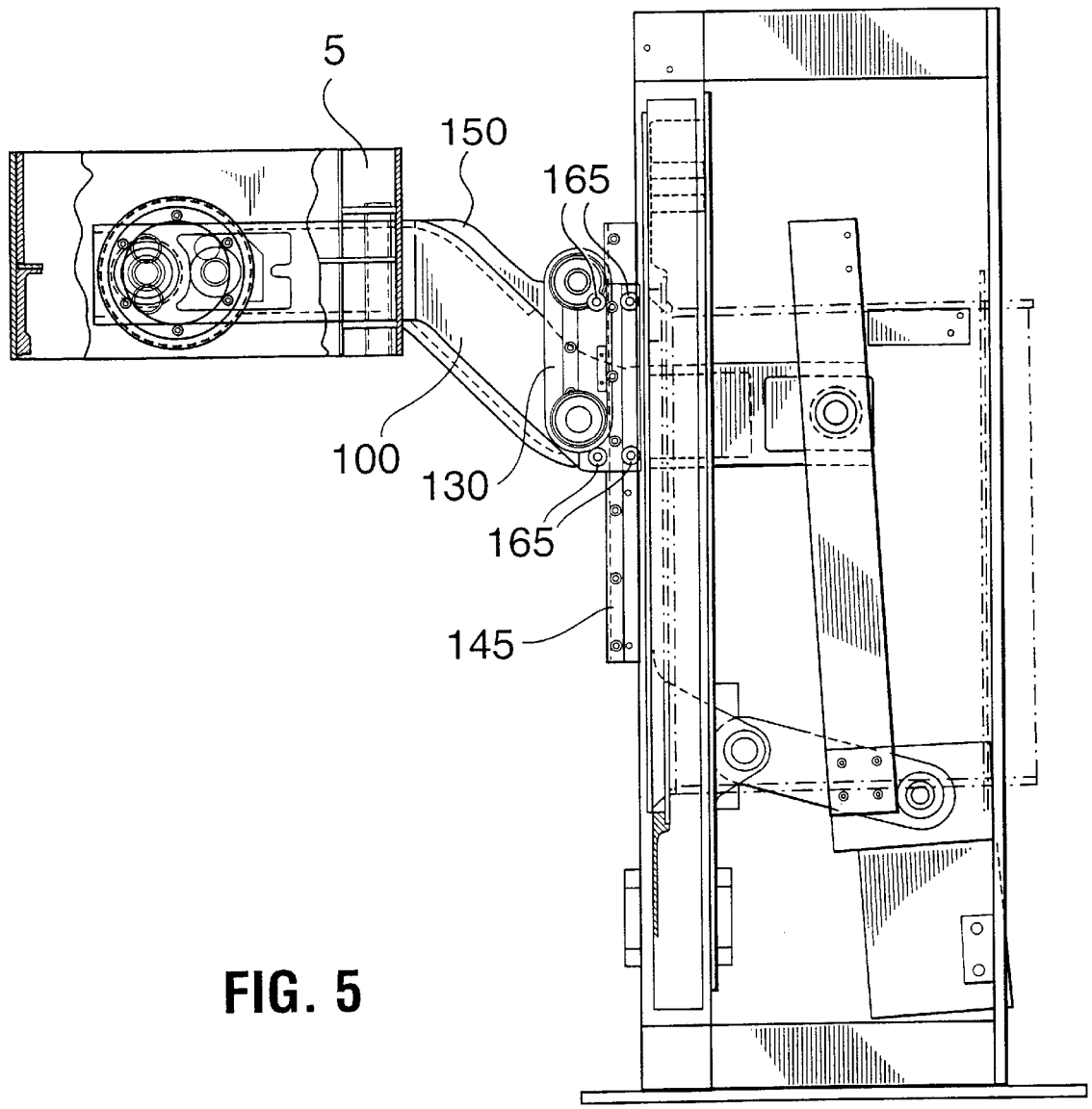
FIG. 5 is a side elevation view of a scintillation camera.
Figure 6:
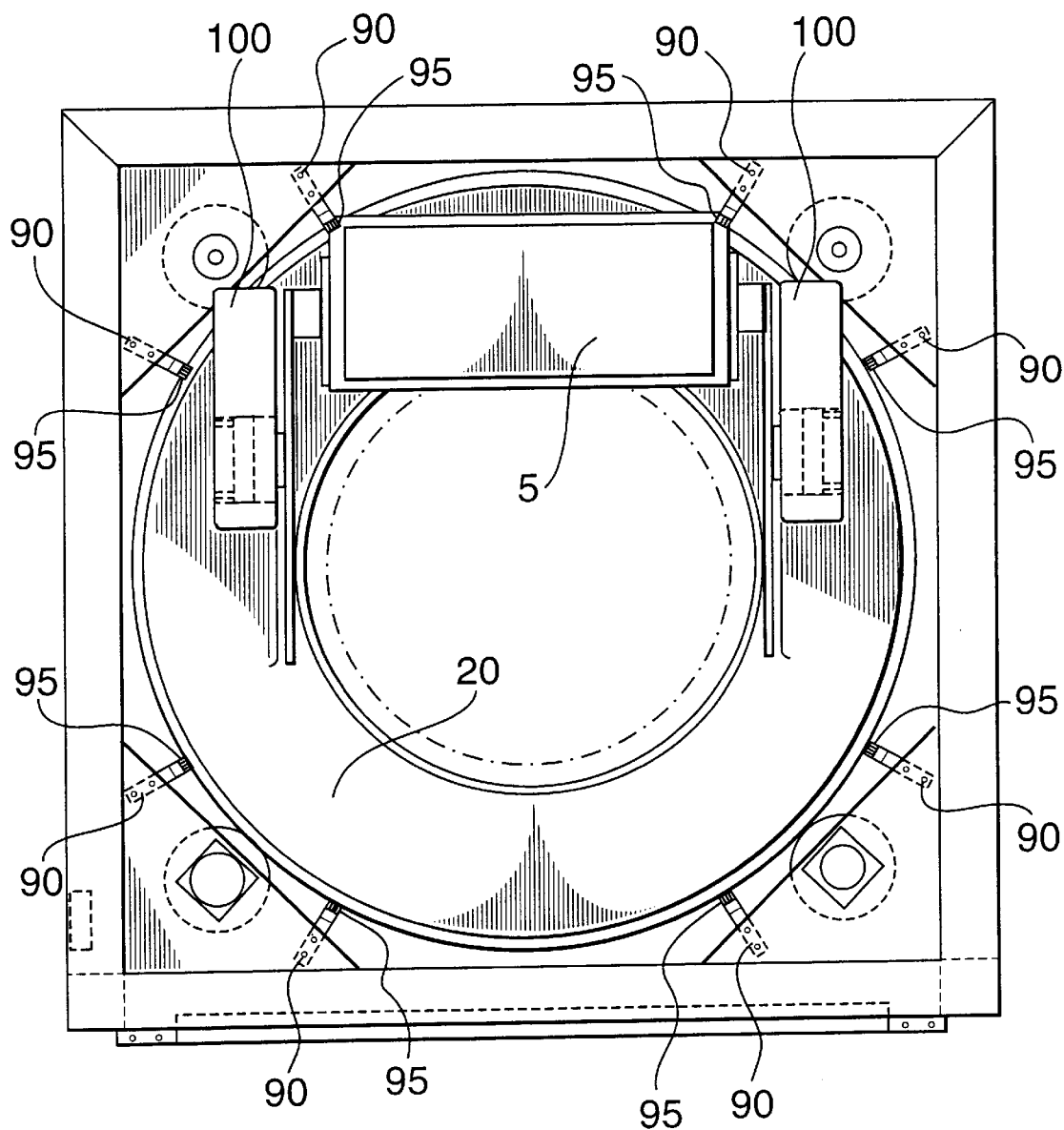
FIG. 6 is a front elevation view of a scintillation camera.
Figure 7:
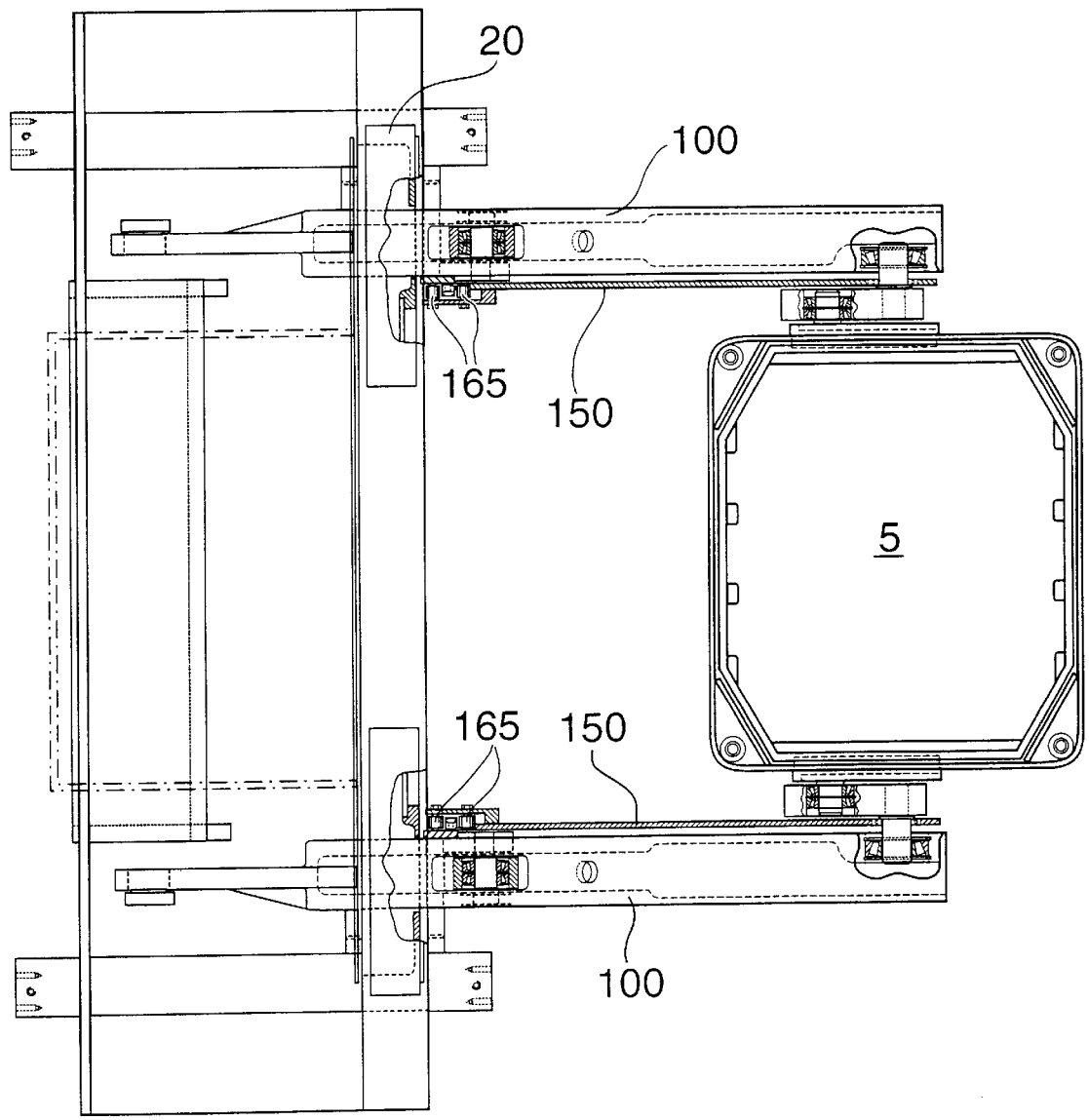
FIG. 7 is a top plan view of a scintillation camera.
Figure 8:
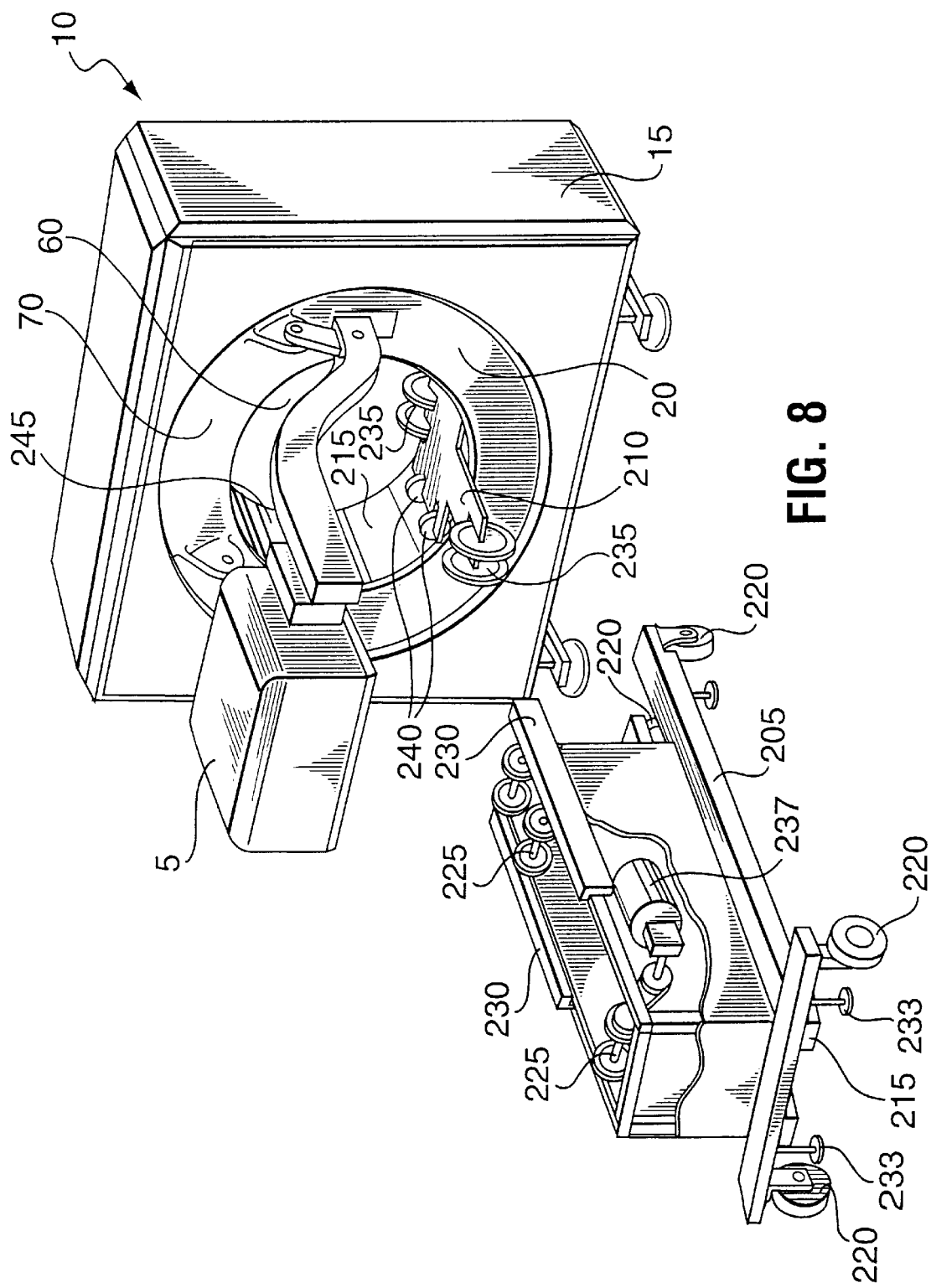
FIG. 8 is a perspective view of the scintillation camera of FIG. 1, including the detached patient support and engaged patient support, with the stretcher removed.
Figure 9:
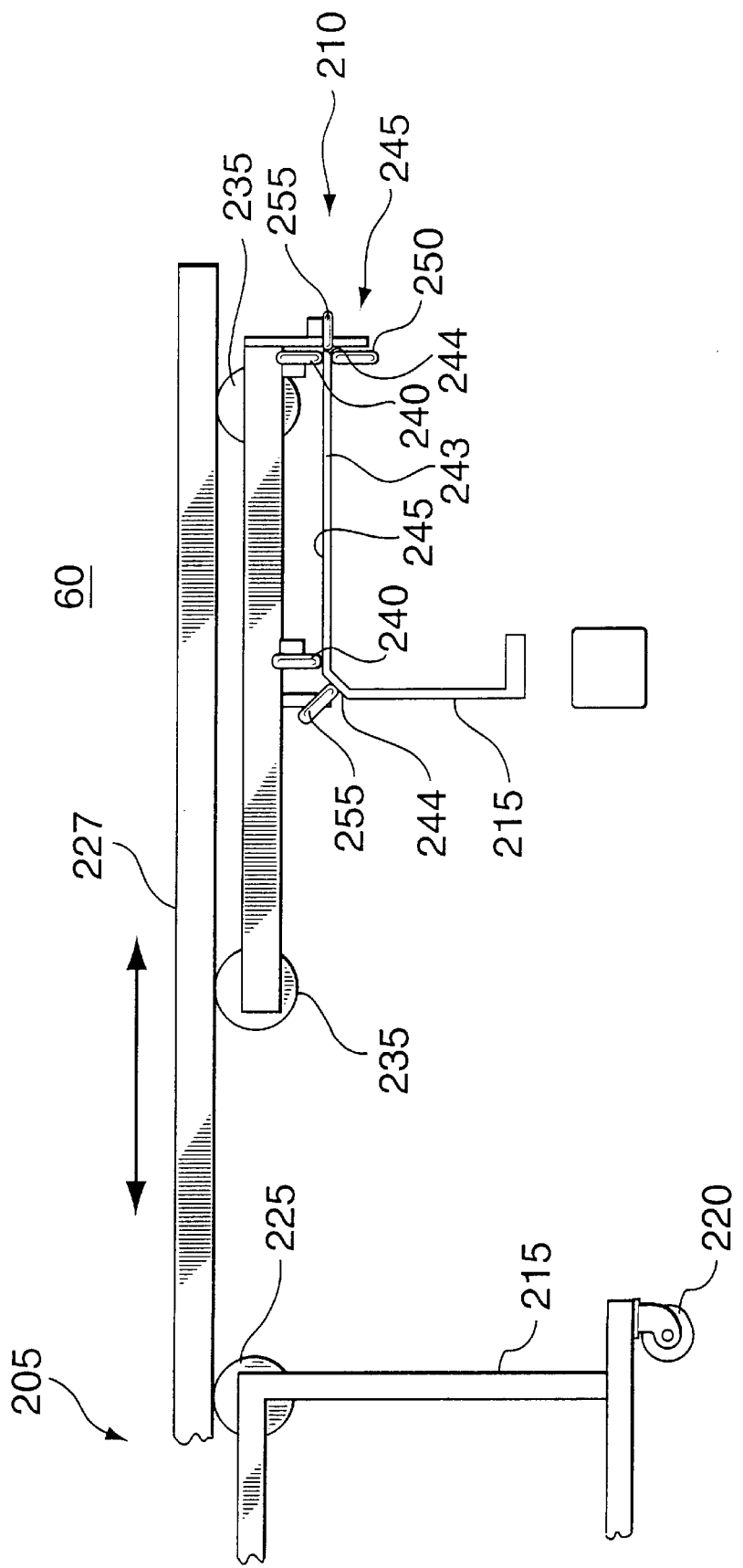
FIG. 9 is a side view of a portion of the patient support apparatus of the present invention.
Figure 10:
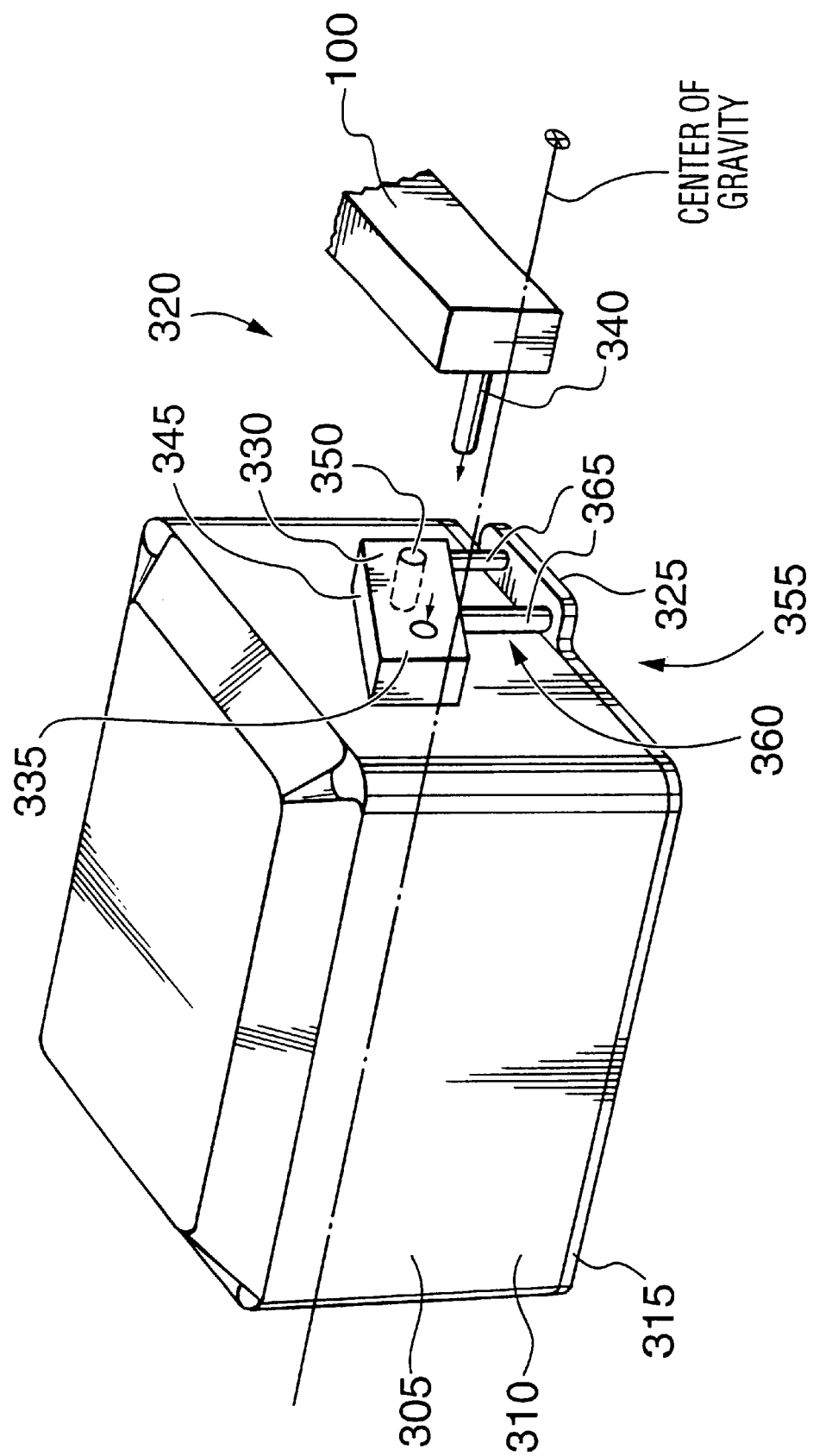
FIG. 10 is a perspective view of the positioner.
Figure 11:
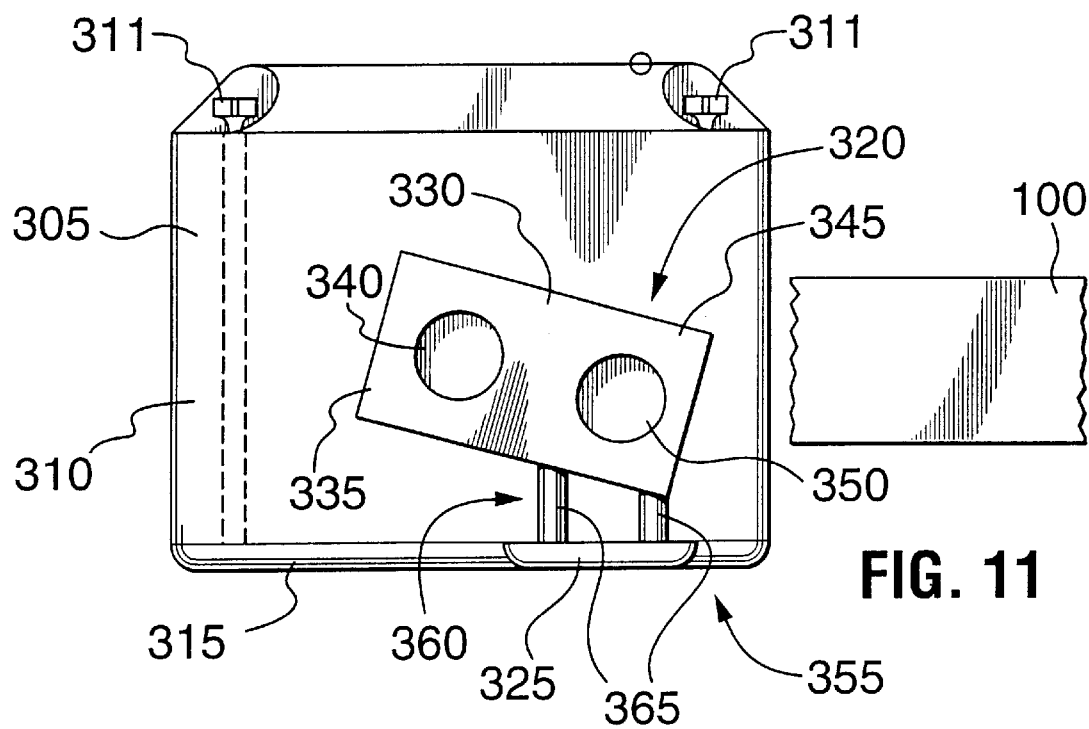
FIG. 11 is a side elevation view of the positioner.
Figure 12:
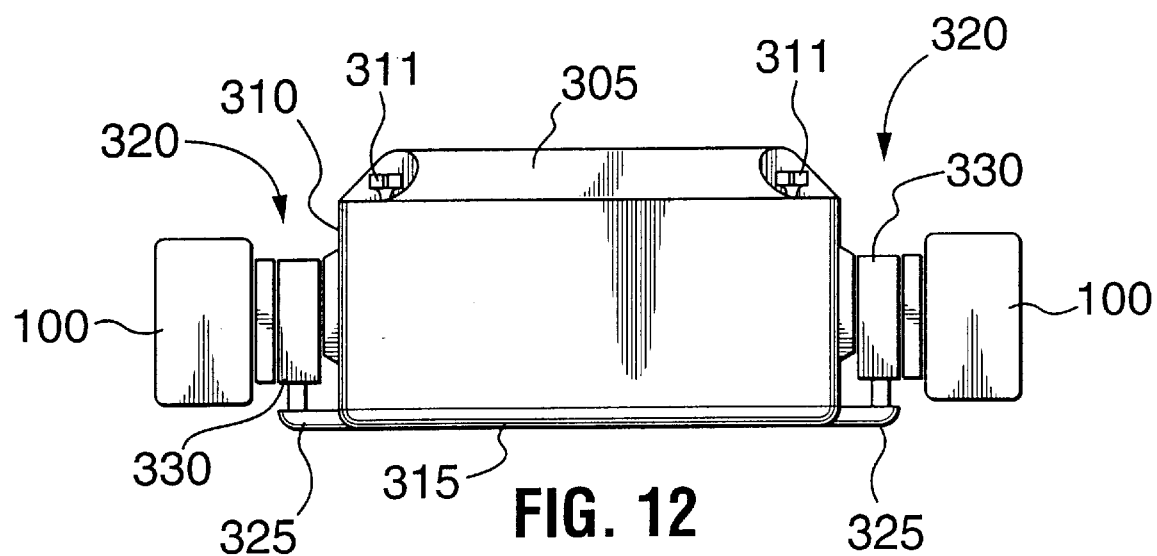
FIG. 12 is a front elevation view of the positioner.

Similar references are used in different figures to denote similar components.

DETAILED DESCRIPTION OF THE INVENTION

Referring to FIGS. 1 to 12, a nuclear camera 5 is supported and positioned relative to a patient by a support structure 10. Nuclear cameras are heavy, usually weighing approximately three to four thousand pounds. Thus, the support structure 10 should be strong and stable in order to be able to position the camera 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. In the illustrated embodiment, the frame 35 is approximately five feet wide, five feet high, and two feet deep. The frame 35 also includes eight triangular corner braces 40 welded to the front square section 37, that is, each corner of the front square section 37 has two corner braces 40, one towards the front of the front square section 37, and one towards the rear of the front square section 37. In the illustrated embodiment, the corner braces 40 are in the shape of equilateral right angle triangles.

Attached to the underside of the frame 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be levelled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. In the illustrated embodiment, the annular support 20 has an outside diameter of about fifty two inches. The annular support 20 is supported by upper rollers 80 and lower rollers 85 which are mounted on the base 15. The upper rollers 80 and lower rollers 85 roll on the outer surface 65, thus enabling the annular support 20 to rotate relative to the base 15 in the plane defined by the annular support 20. Each of the upper rollers 80 and lower rollers 85 are mounted onto a pair of corner braces 40 by way of axles with deep groove bearings. The bearings should be low friction and be able to withstand heavy loads. The axles of the upper rollers 80 are radially adjustable relative to the annular support 20, so that the normal force exerted by the upper rollers 80 on the outer surface 60 is adjustable. The curved surfaces of the upper rollers 80 and lower rollers 85 (i.e. the surfaces that contact the outer surface 60) should be tough so as to be able to withstand the pressures exerted by the annular support 20, and should have a fairly high coefficient of friction so as to roll consistently relative to the annular support 20.

Attached to each pair of corner braces 40 is a stabilizing arm 90 oriented perpendicularly to the plane of the annular support 20. A pair of small stabilizing rollers 95 are mounted onto each stabilizing arm 90. Each pair of stabilizing rollers 95 is positioned such that one stabilizing roller 95 rolls on the front surface 70, and the other stabilizing roller 95 rolls on the rear surface 70. The stabilizing rollers 95 maintain the annular support 20 in the vertical plane.

The elongate support 25 includes a pair of support arms 100, each of which extends through an aperture in the annular support 20. The nuclear camera 5 is rotatably attached to one end of the pair of support arms 100, such that the nuclear camera 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counter weight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counter weight member 110. Each counter weight link 121 is pivotally attached at its other end to a counter weight bracket 122 which is rigidly attached to the annular support 20. The counter weight links 121 are attached to the counterweight members 110 and counter weight brackets 122 using bolts and tapered roller bearings. Each counter weight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera 5, relative to the annular support 20. A pair of brackets 125 is rigidly attached to the annular support 20. A pair of rigid links 130 is pivotally attached at support arm pivot points 135 to the support arms 100. The pair of links 130 is also pivotally attached at bracket pivot points 140 to the brackets 125. At the support arm pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera 5. Each straight end 160 includes a pair of spaced apart cam followers or guides 165 slidable within the corresponding track 145. Thus, movement of the scintillation camera 5 relative to the annular support 20 (i.e. we are not concerned, at this point, with rotational movement of the scintillation camera 5 relative to the elongate support 25) is linear and parallel to the plane of the annular support 20. Note that if the camera ends 155 were pivotally attached to the support arms 100 between the nuclear camera 5 and the annular support 20, the movement of the nuclear camera 5 relative to the annular support 20 would not be linear.

Movement of the scintillation camera 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 of the illustrated embodiment is designed to operate with an apparatus for supporting and positioning a patient, such apparatus including a detached patient support 205, an engaged patient support 210, and a cylinder 215.

The detached patient support 205 includes rigid patient frame 215 supported by four casters 220. Mounted near the top of the patient frame 215 are first support wheels 225 for supporting a stretcher 227 upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera 5 and support structure 10 therefor, and for supporting and positioning a patient relative to the base 15 during operation of the scintillation camera 5 and support structure 10. To ensure that the detached patient support 205 remains stationary during operation of the scintillation camera 5, four stabilizers 233 can be lowered. Thus lowered, the stabilizers 233 ensure that the detached patient support remains stationary relative to the floor.

The engaged patient support 210 includes second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 215 is rigidly mounted to the annular support 20. The cylinder 215 is aligned with the orifice 60 of the annular support 20 such that the cylinder is coaxial with the annular support 20. The cylinder 215 includes a smooth inner surface 245 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 245. The stabilizer 245 includes outside wheels 250 to maintain the engaged patient support 210 horizontal, that is, to stop the engaged patient support from tipping relative to the cylinder 215. The outside wheels 250 roll on the outside surface 243 of the cylinder 215. The stabilizer 245 also includes end wheels 255 to prevent the engaged patient support 210 from moving in a direction parallel to the axis of the cylinder 215. The end wheels 255 roll on the ends 244 of the cylinder 215.

A detector head 305 of the nuclear camera 5 is supported between the two support arms 100 by a positioner 320. The detector head 305 includes a casing 310 in which is contained a scintillation crystal and photomultiplier tubes. Attached to the underside of the casing 310 is a collimator plate 315. The collimator plate 315 is made of lead perforated by narrow channels, and includes a collimator support 325 extending from the two edges of the collimator plate adjacent the support arms 310. The collimator plate 315 is attached to the casing 310 by way of bolts 311. By removing the bolts 311, the collimator plate 315 can be removed from the casing 310 and replaced by another collimator plate 315.

A particular design and weight of collimator is selected depending on the isotope being used or the type of study being conducted. Thus, the collimator plate 315 must be changed from time to time. Since the collimator plates 315 vary considerably in weight from one to another, the location centre of gravity of the detector head 305 is dependent upon the weight of the collimator plate 315 attached to the casing 310. Since the angle of the detector head 305 relative to the patient must be adjusted by an operator of the nuclear camera 5, the detector head 305 must be rotatable relative to the arms 100. If the centre of gravity of the detector head 305 is positioned approximately on the axis of rotation of the detector head relative to the support arms 100, then the detector head 305 will be balanced, and the angle of the detector head 305 relative to the support arms 100 will be adjustable by hand. However, changing the collimator plates moves the centre of gravity of the detector head. Since collimator plates 315 are so heavy, it becomes inconvenient or impossible to adjust the angle of the detector head 305 by hand. The positioner 320 enables the operator to adjust the position of the centre of gravity of the detector head 305 to be approximately aligned with the point of rotation of the detector head 305, which passes through the support arms 100.

The positioner 310 attaches the detector head 305 to the support arms 100 and includes a pair of rigid elongate detector head links 330 for aligning the centre of gravity of the detector head 305 relative to the support arms 100. Each detector head link 330 is rotatable relative to the support arms 310 in a plane substantially parallel to its adjacent support arm 310. Each detector head link 330 includes an arm end 335 rotatably attached to the adjacent support arm 100 by way of an arm axle 340. Each detector head link 330 also includes a head end 345 rotatably attached to the detector head 305 by way of a head axle 350.

The positioner 310 also includes a pair of locks 355 for selectively preventing rotation of the detector head 305 relative to the detector head links 330. Each lock 355 includes the collimator support 325 extending from the detector head 305 from the collimator plate 315. Each lock 355 also includes a block 360 for supporting the detector head link 330 on the collimator support 325. Each block 360 includes a pair of pins 365 located either side of the head axle 350.

Figure 13:
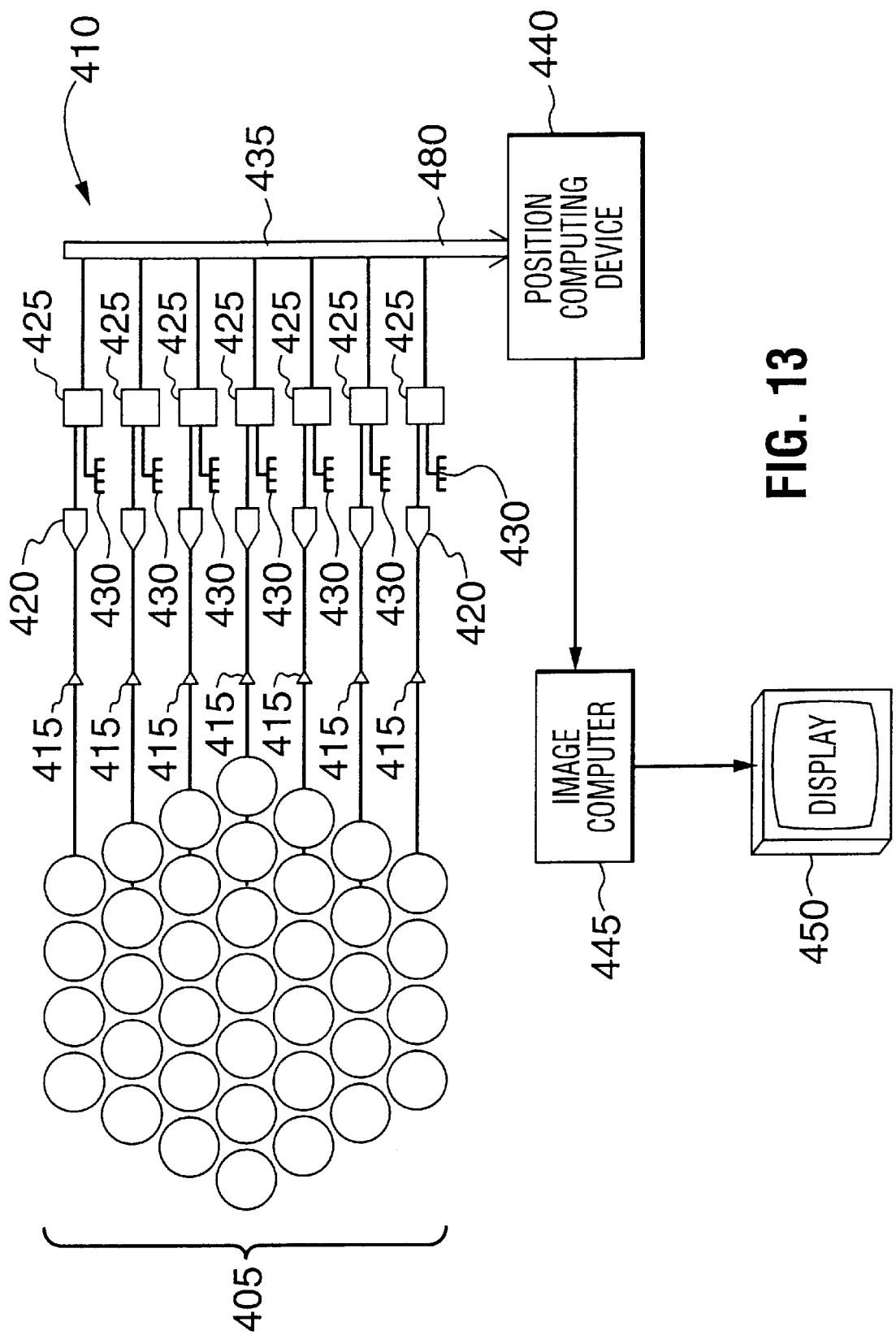
FIG. 13 is a drawing of an embodiment of the photomultiplier tube identifier of the present invention.
Figure 14:
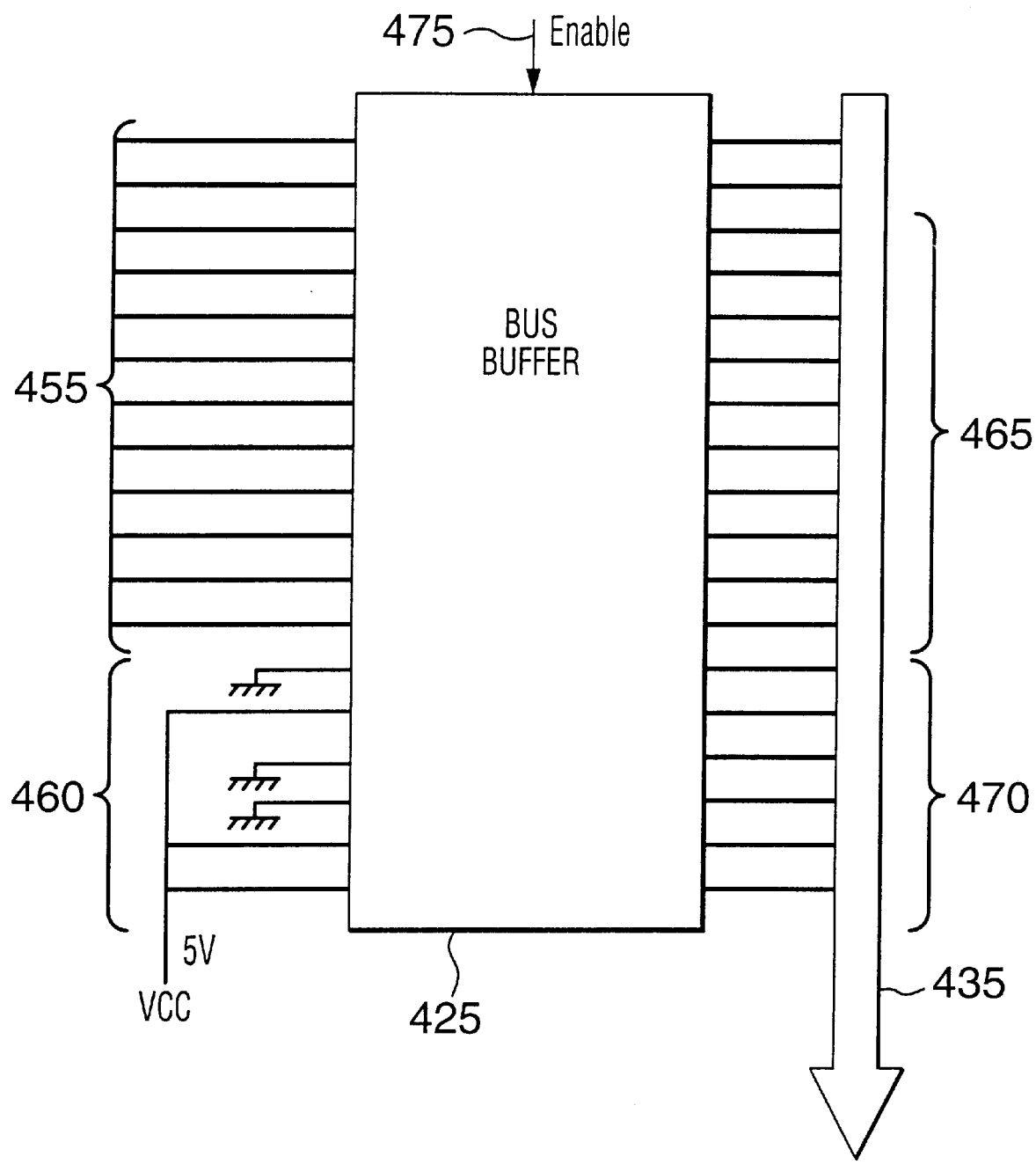
FIG. 14 is a drawing of the bus buffer of the embodiment of FIG. 13.

FIGS. 13 and 14 illustrate an array of photomultiplier tubes 405 in a scintillation camera. A photomultiplier tube identifier 410 is an apparatus for identifying a malfunctioning photomultiplier tube in the array of photomultiplier tubes 405.

The photomultiplier tube identifier 410 includes amplifier/integrators 415, analog to digital converters (ADCs) 420, bus buffers 425, pull-up resistors 430, a bus 435, a position computing device 440, an image computer 445, and a user display 450.

Output signals from individual photomultiplier tubes in the array of photomultiplier tubes 405 are amplified and integrated by the amplifier/integrators 415. The output signals from the amplifier/integrators 415 are then digitized in the analog to digital converters 420. The output signal from a digital to analog converter 420 corresponds to the strength of the signal from an individual photomultiplier tube in the array of photomultiplier tubes 405.

The bus buffers 425 receive outputs signals from the digital to analog converters 420. Some of the gates of the bus buffers 425 are also connected to the pull up resistors 430. The gates of the bus buffer are set by the pull up resistors 430 to a logic high or topic low which correspond to the identities of the individual photomultiplier tubes from which signals have been obtained. To each output signal from the digital to analog converters 420, the bus buffers 425 add a code below the least significant bits identifying the photomultiplier tube from which the signal was obtained. Thus, the output signals from the bus buffers 425 corresponds to the strength of the signals received from the array of photomultiplier tubes 405 plus a code identifying the photomultipliers tube from which the signals were obtained.

FIG. 14 illustrates an eighteen bit bus buffer 425. Output signals 455 from a digital to analog converter 420, in this case twelve most significant bits of signal data, are received by the bus buffer 425. The twelve bit output signals 455 correspond to the specific photomultiplier tube providing the output signal. Logic values 460 from pull up resistors 430, in this case 6 bits of data, provide a hard wired code corresponding to the identity of the specific photomultiplier tube. In this case, as the pull up resistors provide six bits of data, the signals from sixty four different photomultiplier tubes 405 may be encoded.

Upon receipt of the enable command at 475, the data from the bus buffer is read onto the bus 435. The signal values 465, that is, the first twelve bits of data correspond to the output signal received from the digital to analog converter 415. The code values 470, that is, the next six bits of data, provide the code identifying the specific photomultiplier tube 405 providing the information. The signals 460 in FIG. 14 provide a code of 010011, ground being represented by 0 and VCC being represented by 1. If more codes are required, a larger bus buffer can be used, such as a twenty or thirty two bit bus buffer.

Encoded signals 480 are read onto the bus 435. The first twelve bits of each encoded signal 480 are the signals values 465, and the remaining six bits of each encoded signal 480 are the code values 470. The encoded signals 480 are received by the position computing device 440. Since the code values 470 are in the low part of the encoded signal 480 or data word used by the position computing device 440, the change in value created by adding the code values 470 to the signal values 470 is negligible. Therefore, the code values 470 do not need to be removed before the encoded signal 480 is used by the position computing device 440. For example, the encoded signal may represent the value 1,001, 325.238. The final two digits, that is, eight and three, may be the code identifying the thirty eighth photomultiplier tube in the array. The 0.038 value could be removed from the encoded signal 480 prior to processing by the position computing device 440. However, such a calculation would not be beneficial as the 0.038 a negligible value compared with the value 1,001,325.238. If an artifact appears on the generated image, and the artifact can be traced to the data value 1,001,325.238, then photomultiplier tube number thirty eight can be repaired or replaced. Similarly, if an artifact appears on the generated image, and fewer data values traceable to photomultiplier tube number thirty eight than are statistically expected, then photomultiplier tube number thirty eight may need repairing or replacing.

In this way, the position computing device 440 can transmit information to the image computer 445 and then the display 450 quickly and inexpensively while retaining intact information identifying the specific photomultiplier tubes corresponding the specific data.

Numerous modifications, variations and adaptations may be made to the particular embodiments of the invention described above without departing from the scope of the invention, which is defined in the claims.

I claim:

1. An apparatus for identifying an event in a scintillation camera comprising an array of photomultiplier tubes, each photomultiplier tube generating a photomultiplier tube signal, comprising:

(a) means for generating a code signal identifying each of the photomultiplier tubes in the array;

(b) a bus buffer for transmitting an encoded signal comprising the photomultiplier tube signal followed by the code signal;

(c) a position computing device for calculating the position of the event from the encoded signal, the code signal being negligible relative to the encoded signal so as not needing to be removed from the encoded signal when the encoded signal is used by the position computing device;

(d) an image computer for generating an image from a plurality of encoded signals; and (e) a display for displaying the image.

2. An apparatus as defined in claim 1, further comprising:

(a) an amplifier/integrator for generating an amplified/integrated signal from the photomultiplier tube signal; and (b) an analog to digital converter for generating a digitized signal from the amplified/integrated signal.

3. An apparatus as defined in claim 2, wherein the event is a malfunctioning photomultiplier tube.

4. An apparatus as defined in claim 3, wherein the means for generating the code signal identifying each of the photomultiplier tubes comprises a series of pull up resistors.

5. An apparatus as defined in claim 4, wherein the size of the bus buffer depends upon the number of code signals required.

6. A method for identifying an event in a scintillation camera comprising an array of photomultiplier tubes, comprising the steps of:

(a) generating a photomultiplier tube signal for each of the photomultiplier tubes in the array;

(b) generating a code signal identifying each of the photomultiplier tubes in the array;

(c) generating an encoded signal comprising the photomultiplier tube signal followed by the code signal;

(d) calculating the position of the event using the encoded signal, the code signal being negligible relative to the encoded signal so as not needing to be removed from the encoded signal prior to calculating the position of the event;

(e) generating an image from a plurality of encoded signals; and (f) displaying the image.

7. A method as defined in claim 6, further comprising the steps of:

(a) generating an amplified/integrated signal from the photomultiplier tube signal; and (b) generating a digitized signal from the amplified/integrated signal.

8. A method as defined in claim 7, wherein the event is a malfunctioning photomultiplier tube.

9. An apparatus for identifying a malfunctioning photomultiplier tube in a scintillation camera comprising an array of photomultiplier tubes, each photomultiplier tube generating a photomultiplier tube signal, comprising:

(a) means for generating a code signal identifying each of the photomultiplier tubes in the array;

(b) means for generating an encoded signal comprising the photomultiplier tube signal followed by the code signal;
(c) means for calculating the position of the malfunctioning photomultiplier tube using the encoded signal, the code signal being negligible relative to the encoded signal so as not needing to be removed from the encoded signal when the encoded signal is used by the means for calculating the position of the malfunctioning photomultiplier tube;
(d) means for generating an image from a plurality of encoded signals; and
(e) means for displaying the image.

10. An apparatus as defined in claim 9, further comprising:
(a) means for generating an amplified/integrated signal from the photomultiplier tube signal; and
(b) means for generating a digitized signal from the amplified/integrated signal.

11. An apparatus as defined in claim 10, wherein:
(a) the means for generating the amplified/integrated signal from the photomultiplier tube signal comprises an amplifier/integrator;
(c) the means for generating the digitized signal from the amplified/integrated signal comprises an analog to digital converter;
(d) the means for generating the code signal identifying each of the photomultiplier tubes in the array comprises a series of pull up resistors;
(e) the means for generating the encoded signal comprising the photomultiplier tube signal followed by the code signal comprises a bus buffer;
(f) the means for calculating the position of the malfunctioning photomultiplier tube comprises a position computing device;
(g) the means for generating the image from a plurality of encoded signals comprises an image computer; and
(h) the means for displaying the image comprises a display.

12. A scintillation camera comprising:
(a) a detector including an array of photomultiplier tubes, each photomultiplier tube generating a photomultiplier tube signal; and
(b) an apparatus for identifying a malfunctioning photomultiplier tube in the array, the apparatus comprising:
  (i) means for generating a code signal identifying each of the photomultiplier tubes in the array;
  (ii) a bus buffer for transmitting an encoded signal comprising the photomultiplier tube signal followed by the code signal;
  (iii) a position computing device for calculating the position of malfunctioning photomultiplier tube from the encoded signal, the code signal being negligible relative to the encoded signal so as not needing to be removed from the encoded signal when the encoded signal is used by the position computing device;
  (iv) an image computer for generating an image from a plurality of encoded signals; and
  (v) a display for displaying the image.

13. A scintillation camera as defined in claim 12, wherein the detector further includes:
(i) a collimator for collimating gamma rays; and
(ii) a scintillator for absorbing the gamma rays and producing a flash of light, the flash of light being converted into the photomultiplier tube signal in the photomultiplier tubes.

14. A scintillation camera as defined in claim 12, wherein the apparatus further includes
(i) an amplifier/integrator for generating an amplified/integrated signal from the photomultiplier tube signal; and
(ii) an analog to digital converter for generating a digitized signal from the amplified/integrated signal.

15. A scintillation camera as defined in claim 12, wherein the means for generating the code signal identifying each of the photomultiplier tubes comprises a series of pull up resistors.

* * * * *